United States Patent [19]

Anderson

[11] Patent Number: 4,500,290
[45] Date of Patent: Feb. 19, 1985

[54] ARTICULATOR DEVICE AND METHOD

[76] Inventor: Jerry C. Anderson, 4567 W. Central, Suite B, Wichita, Kans. 67212

[21] Appl. No.: 502,762

[22] Filed: Jun. 9, 1983

[51] Int. Cl.³ .............................................. A61C 11/00
[52] U.S. Cl. ......................................... 433/54; 433/65
[58] Field of Search ....................... 433/54, 55, 56, 57, 433/58, 59, 60, 61, 62, 63, 64, 65, 66, 67

[56] References Cited

U.S. PATENT DOCUMENTS

| | | | |
|---|---|---|---|
| 2,510,152 | 6/1950 | Stoll | 433/65 |
| 2,617,195 | 11/1952 | Perkell et al. | 433/65 |
| 2,670,538 | 3/1954 | Thompson | 433/55 |
| 2,816,360 | 12/1957 | Stuart | 433/55 |
| 4,412,822 | 11/1983 | Blechner | 433/59 |

FOREIGN PATENT DOCUMENTS

| | | | |
|---|---|---|---|
| 448368 | 5/1948 | Canada | 54/ |
| 960846 | 4/1950 | France | 433/65 |

*Primary Examiner*—John J. Wilson
*Attorney, Agent, or Firm*—John H. Widdowson

[57] ABSTRACT

An articulator device for articulating upper and lower dental casts comprising a base having a generally T-shaped structure defining a tongue-like protrusion including a longitudinal slot. A lower dental cast holding pad is secured to the tongue-like protrusion and is movably disposed along the longitudinal slot for an anterior-posterior direction reposition of the lower dental cast with respect to the upper dental cast for malocclusive correction. A pair of support pins are implanted in the base. A pair of collars are slideably positioned along the support pins and have a pair of thumb bolts for fixedly securing the collars to the support pins. A guide member is slideable along the support pins and is supported by the collars to elevate or lower the guide member in accordance with the movements of the collar. A holder is supported by the guide member and has a generally T-shaped structure defining a tongue-like protrusion. The holder is capable of being laterally moved with respect to the guide member. An upper dental cast holding pad is bound to the tongue-like protrusion of the holder.

3 Claims, 5 Drawing Figures 4,500,290

ARTICULATOR DEVICE AND METHOD

BACKGROUND OF THE INVENTION

1. Field of the Invention

This invention is related to an articulator means and method. More specifically, this invention provides an articulator apparatus and method that is used in a dental laboratory by a dentist or dental technician to articulate dental casts which the technician has made from mouth impressions furnished by the dentist.

2. Description of the Prior Art

U.S. Pat. No. 3,758,096 by Tregillis et al discloses an articulator that illustrates an arrangement for holding dentures and has an adjustment which is apparently only vertical. U.S. Pat. No. 2,534,023 by Hirschorn discloses an articulator wherein the dentures may be supported for pivotal or universal adjustment with respect to each other. U.S. Pat. No. 2,952,914 by Shackelford discloses an arrangement wherein the dentures may be primarily vertically adjusted relative to one another. U.S. Pat. No 2,816,360 by Stuart illustrates an articulator wherein both vertical and a relative adjustment between the denture assemblies may be accomplished. U.S. Pat. No. 2,765,533 by McMorris also illustrates an articulator supporting a pair of dentures so that the denture assemblies, both upper and lower, may be adjusted vertically and also angularly by the means of this structure. None of the foregoing prior art teaches or suggests the particular articulator apparatus and method of this invention.

SUMMARY OF THE INVENTION

This invention accomplishes its desired objects by providing a novel articulator device for articulating upper and lower dental casts comprising a base having a generally T-shaped structure defining a tongue-like protrusion including a longitudinal slot and a lower dental cast holding pad means for holding said lower dental cast and secured to the tongue-like protrusion and movably disposed along the longitudinal slot for anterior-posterior direction reposition of the lower dental cast with respect to the upper dental cast for malocclusive correction. A pair of support pins means is implanted in the base. A pair of collar means are slideably positioned along the support pins means and has means for fixedly securing the collar means to the support pins means. A guide member means is slideably disposed along the support pins means and is supported by the collars means in order to be elevated or lowered in accordance with the movements of the collar means. A holder means is supported by the guide member means and has a generally T-shaped structure defining a tongue-like protrusion. The articulator device additionally comprises means for adjustably laterally moving the holder means with respect to the guide member means to align the upper and lower dental casts for posterior occlusion, and an upper dental cast holding pad means for holding the upper dental cast and rotatably bound to the tongue-like protrusion of the holder means. This invention additionally accomplishes its desired objects by providing a method for articulating upper and lower dental casts which comprises the steps of positioning the lower dental cast in a lower dental cast holding pad means and positioning the upper dental cast in an upper dental cast holding pad means; and lowering the combined upper dental cast holding pad means and upper dental cast towards the combined lower dental cast holding pad means and lower dental cast in order to vertically adjust the upper dental cast with respect to the lower dental cast. The combined upper dental cast pad means and lower dental cast are laterally moved in order to align for any posterior occlusion, and the combined lower dental cast pad means and lower dental cast are repositioned in an anterior-posterior direction for malocclusive correction.

It is an object of this invention to provide a method for articulating upper and lower dental casts, and an articulator device which is capable of easily being assembled, adjusted and stored.

It is another object of this invention to provide a method of articulating upper and lower dental casts, and an articulating device which is capable of vertically adjusting the dental cast in a fixed perpendicular plane, laterally moving the dental cast to align for any posterior occlusion, and repositioning the lower dental cast in an anterior-posterior direction for malocclusive correction.

Still further objects of the invention reside in the provision of an articulative device which can be easily transported and is relatively inexpensive to manufacture.

These, together with the various ancillary objects and features will become apparent as the following description proceeds, are attained by this invention, preferred embodiments being shown in the accompanying drawings, by way of example only, wherein:

DETAILED DESCRIPTION OF THE INVENTION

Figure 1:
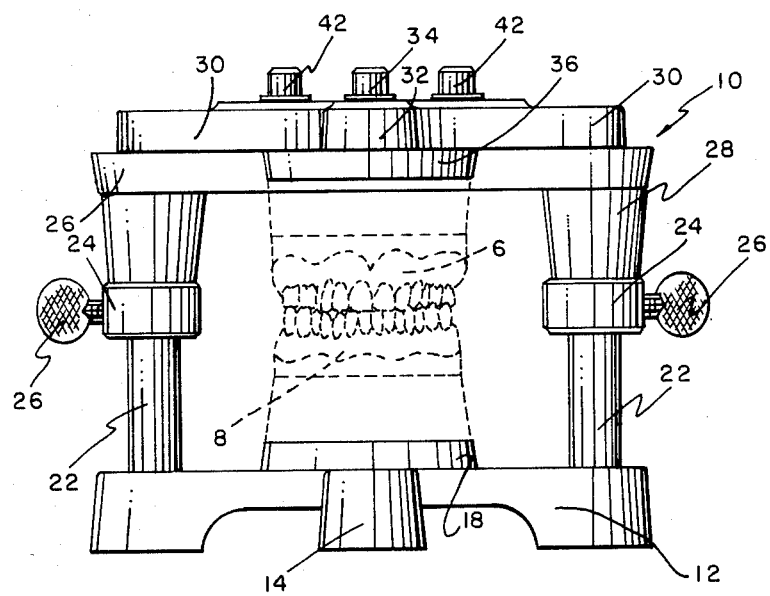
FIG. 1 is a front elevational view of the articulator device with the upper and lower dental casts being represented by dotted lines.
Figure 2:
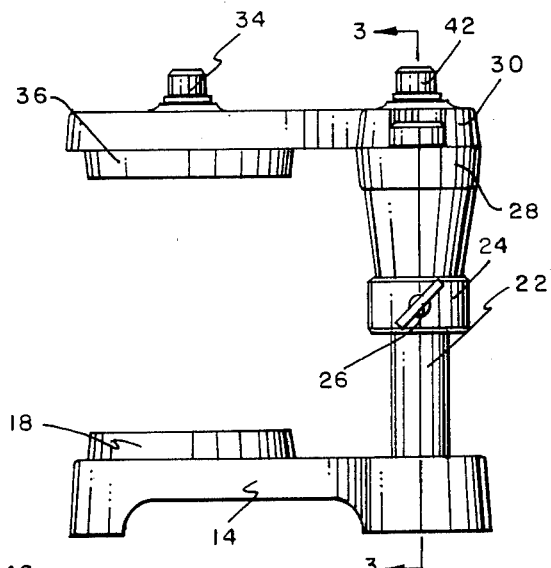
FIG. 2 is a side elevational view of the articulator device.
Figure 3:
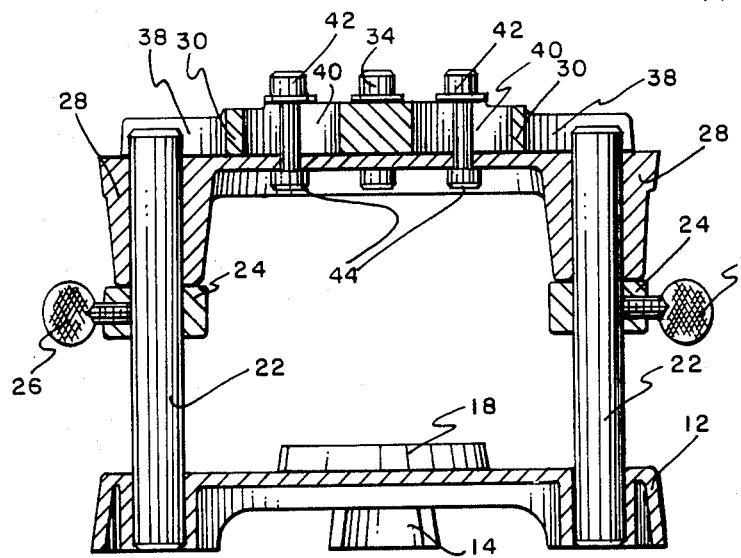
FIG. 3 is a vertical sectional view taken in direction of the arrows and along the plane of line 3—3 in FIG. 2.
Figure 4:
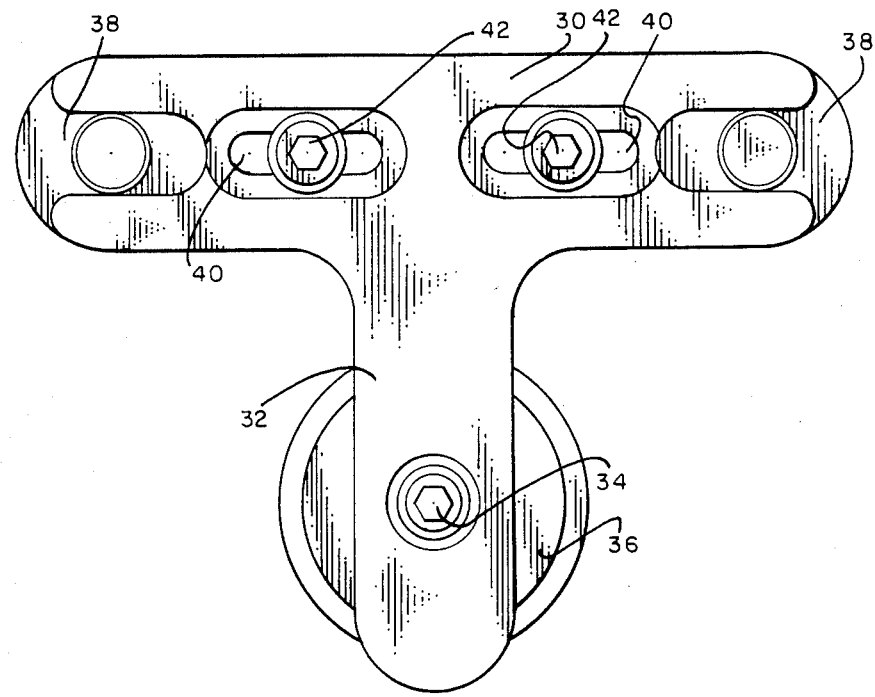
FIG. 4 is a top plan view of the articulator device.
Figure 5:
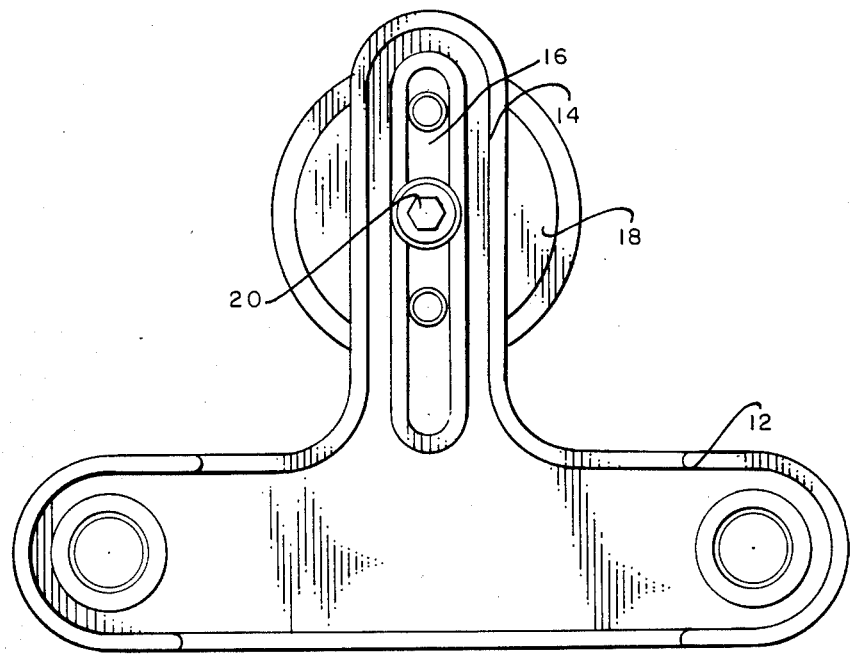
FIG. 5 is a bottom plan view of the articulator device.

Referring in detail now to the drawings wherein similar parts of the invention are identified by like reference numerals, there is seen the articulator device, generally illustrated as 10, for articulating upper 6 and lower dental casts 8 which were made from the mouth impressions furnished by the dentist, having a T-shaped base 12 with a tongue-like protrusion 14 which has a longitudinal slot 16. A lower dental cast holding pad 18 holds the lower dental cast 8 and is secured to the tongue-like protrusion 14 by a bolt 20. By loosening the bolt 20 the lower dental cast holding pad 18 with the lower dental cast 8 is movably disposed along the longitudinal axis of the slot 16 for anterior-posterior direction repositioning of the lower dental cast 8 with respect to the upper dental cast 6 for malocclusive correction. A pair of support pins 22—22 are implanted in the base 12. A pair of collars 24—24 are slidably positioned around and along the support pins 22—22 and each collar 24 has a thumb bolt 26 for securing the collars 24—24 to the support pins 22—22. A guide member 28 is slidably disposed along the pair of support pins 22—22 and is supported by the pair of collars 24—24 in order to be elevated or lowered in accordance with the movements of the collars 24—24. A T-shaped holder 30 is connected to and supported by guide member 28. Holder 30 has a tongue-like protrusion 32 wherein a bolt 34 fastens an upper dental cast holding pad 36 which holds the upper dental cast 6. Upper dental cast holding pad 36 can be rotated to finely adjust the upper dental cast 6 with respect to the lower dental cast 8.

Holder 30 has a structure defining a pair of generally elongated recessed apertures 38—38 through which the top of the support pins 22—22 slideably pass. Holder 30 additionally includes a pair of elongated slots 40—40 through which a pair of bolts 42—42 pass to be rotatably or threadably connected to the guide member 28. In a preferred embodiment of the invention, nuts 44—44 may be utilized to also enable the bolts 42—42 to affix the holder 30 and the guide member 28 together. By loosening the bolts 42—42 threadably engaged into guide member 28, or the nuts 44—44 of bolts 42—42, the holder 30 can be laterally adjusted and moved along the longitudinal axis of its elongated slots 40—40. By loosening and tightening the bolts 42—42 along the longitudinal axis of the elongated slots 40—40 of the holder 30, a means is provided for adjustably laterally moving the holder 30 with respect to the guide member 28 to align the upper 6 and lower dental cast 8 for posterior occlusion.

With continuing reference to the drawings for operation of the invention and the method for articulating the upper 6 and lower dental casts 8 which were made from a mouth impression furnished by the dentist, the lower 8 and upper dental casts 6 are positioned in the lower dental cast holding pad 18 and the upper dental cast holding pad 36, respectively. The thumb bolts 26—26 are loosened to slide downwardly the collars 24—24 and the guide member 28; this lowers the combined upper pad 36-upper dental cast 6 towards the combined lower pad 18-lower dental casts 8 in order to vertically adjust the upper dental cast 6 with respect to the lower dental cast 8. The upper dental cast holding pad 36 may be rotated by loosening bolt 34 to finely adjust the dental casts 6 and 8 with respect to each other. Bolts 42—42 may be loosened to laterally move the holder 30 and the attached upper dental cast holding pad 36 with respect to lower dental cast 8 in order to align the dental casts 6 and 8 for any posterior occlusion. The holder 30 (and the combined holding pad 36 and upper dental cast 6) can be laterally adjusted and moved by loosening and tightening the connecting bolts 42—42 along the longitudinal axis of the elongated slots 40—40 of the holder 30. Malocclusive correction of the dental casts 6 and 8 is accomplished by loosening (and tightening) the bolt 20 and repositioning the unbound lower dental cast pad 18-lower dental cast 8 in an anterior-posterior direction along the longitudinal axis of the slot 16 of the tongue-like protrusion 14 of the T-shaped base 14. Thus by the practice of this invention the dental casts 6 and 8 produced by the dental technician are articulated, and when done, are used to determine what dental orthopedic appliances are needed to correct abnormalities and to design and construct the orthopedic appliances. By grinding the base of the upper 6 and lower dental casts 8 parallel to the occlusal plane, or having both bases of the upper 6 and lower dental casts 8 parallel to each other with the wax bite, the articulator device 10 enables the operator to change the vertical in a fixed perpendicular plane, to align the models in a horizontal plane through lateral movement of the articulator 10 in order to align the posterior occlusion to reposition the models in an anterior-posterior direction for the correction of class U malocclusion, and to rotate the upper model to align the midline. The articulator device 10 is used mainly to set bites for temple mendablur joints splints or any orthodontic or orthopedic appliances requiring occlusal pads and all functional appliances.

While the present invention has been described herein with reference to particular embodiments thereof, a latitude of modification, various changes and substitutions are intended in the foregoing disclosure, and it will be appreciated that in some instances some features of the invention will be employed without a corresponding use of other features without departing from the scope of the invention as set forth.

I claim:

1. An articulator device for articulating upper and lower dental casts comprising a base having a generally T-shaped structure defining a tongue-like protrusion including a longitudinal slot;

a lower dental cast holding pad for holding said lower dental cast and secured to the tongue-like protrusion and movably disposed along said longitudinal slot for anterior-posterior direction repositioning of the lower dental cast with respect to the upper dental cast for malocclusive correction;

a pair of support pins implanted in said base;

a pair of collars slideably positioned along the support pins and having means for fixedly securing the collars to the support pins;

a guide member slideably disposed along the pair of support pins and supported by the collars in order to be elevated or lowered in accordance with the movements of the collars;

a holder supported by said guide member and having a generally T-shaped structure defining a tongue-like protrusion, said holder comprising a structure defining a pair of generally elongated recessed apertures wherethrough said pair of pins slideably pass and said holder further defining a pair of elongated slots;

means for adjustably laterally moving said holder with respect to said guide member to align the upper and lower dental casts for posterior occlusion;

and an upper dental cast holding pad for holding the upper dental cast and rotatably bound to said tongue-like protrusion of said holder.

2. The articulator of claim 1 wherein said means for adjustably laterally moving comprises a pair of connecting bolts passing through said pair of elongated slots and rotatably into said guide member such that said holder can be laterally adjusted and moved by loosening and tightening the connecting bolts along the longitudinal axis of the elongated slots of said holder.

3. The articulator device of claim 2 wherein said means for fixedly securing of said collars is a pair of thumb bolts.

* * * * *